United States Patent
Nesterenko et al.

(10) Patent No.: US 9,771,307 B2
(45) Date of Patent: Sep. 26, 2017

(54) PROCESS FOR OBTAINING MODIFIED MOLECULAR SIEVES

(71) Applicant: TOTAL RESEARCH & TECHNOLOGY FELUY, Seneffe (Feluy) (BE)

(72) Inventors: Nikolai Nesterenko, Nivelles (BE); Walter Vermeiren, Houthalen (BE); Sander Van Donk, Sainte-Adresse (FR); Delphine Minoux, Nivelles (BE)

(73) Assignee: TOTAL RESEARCH & TECHNOLOGY FELUY, Seneffe (BE)

( * ) Notice: Subject to any disclaimer, the term of this patent is extended or adjusted under 35 U.S.C. 154(b) by 76 days.

(21) Appl. No.: 14/670,277

(22) Filed: Mar. 26, 2015

(65) Prior Publication Data

US 2015/0259264 A1  Sep. 17, 2015

Related U.S. Application Data

(62) Division of application No. 12/811,219, filed as application No. PCT/EP2009/050758 on Jan. 23, 2009, now Pat. No. 9,180,439.

(30) Foreign Application Priority Data

Jan. 25, 2008  (EP) .................... 08150687

(51) Int. Cl.
| | |
|---|---|
| *C07C 1/20* | (2006.01) |
| *C07C 1/207* | (2006.01) |
| *C07C 1/22* | (2006.01) |
| *C07C 4/06* | (2006.01) |
| *B01J 29/06* | (2006.01) |
| *B01J 29/40* | (2006.01) |
| *B01J 37/28* | (2006.01) |
| *B01J 27/16* | (2006.01) |
| *C08F 110/02* | (2006.01) |
| *B01J 37/02* | (2006.01) |

(52) U.S. Cl.
CPC ............... *C07C 1/20* (2013.01); *B01J 27/16* (2013.01); *B01J 29/06* (2013.01); *B01J 29/061* (2013.01); *B01J 29/40* (2013.01); *B01J 29/405* (2013.01); *B01J 37/28* (2013.01); *C07C 4/06* (2013.01); *C08F 110/02* (2013.01); *B01J 37/0201* (2013.01); *B01J 37/024* (2013.01); *B01J 37/0207* (2013.01); *B01J 2229/16* (2013.01); *B01J 2229/186* (2013.01); *B01J 2229/36* (2013.01); *B01J 2229/37* (2013.01); *C07C 2523/02* (2013.01); *C07C 2527/14* (2013.01); *C07C 2529/06* (2013.01); *C07C 2529/40* (2013.01); *C07C 2529/82* (2013.01); *C07C 2529/85* (2013.01); *C10G 2400/20* (2013.01); *Y02P 30/42* (2015.11)

(58) Field of Classification Search
CPC .. C07C 1/20; C07C 1/207; C07C 1/22; C07C 1/24; C07C 4/06
USPC ....... 585/324, 326, 327, 329, 330, 639, 640, 585/653
See application file for complete search history.

(56) References Cited

U.S. PATENT DOCUMENTS 7,230,151 B2 *  6/2007  Martens .................... C07C 1/20
                                                     585/324

* cited by examiner

*Primary Examiner* — Thuan D Dang
(74) *Attorney, Agent, or Firm* — Albert Shung (57) ABSTRACT

A process may include contacting an oxygen-containing, halogenide-containing or sulphur-containing organic feedstock in an XTO reactor with a catalyst composite under conditions effective to convert the oxygen-containing, halogenide-containing or sulphur-containing organic feedstock to olefin products. The catalyst composite may include at least 10 weight percent of a modified molecular sieve. The modified molecular sieve may include at least 0.05 weight percent of an alkaline earth metal or a rare earth metal based on a weight of the modified molecular sieve. The modified molecular sieve may include at least 0.3 weight percent of P based on the weight of the modified molecular sieve.

23 Claims, 1 Drawing Sheet

PROCESS FOR OBTAINING MODIFIED MOLECULAR SIEVES

CROSS-REFERENCE TO RELATED APPLICATIONS

This application is a Divisional of U.S. patent application Ser. No. 12/811,219, filed on Dec. 3, 2010, which is a National Stage Entry of PCT/EP2009/050758, filed on Jan. 23, 2009, which claims priority to EP 08150687.5, filed on Jan. 25, 2008.

FIELD OF THE INVENTION

The present invention relates to modified molecular sieves as well as their use in conversion of organics to light olefins. The invention is useful as a catalyst in a variety of processes including cracking, hydrocracking, isomerization, reforming, dewaxing, alkylation, transalkylation and conversion of oxygenates (or halogenide-containing or sulphur-containing organic compounds) to light olefins.

BACKGROUND OF THE INVENTION

The limited supply and increasing cost of crude oil has prompted the search for alternative processes for producing hydrocarbon products. One such process is the conversion of oxygen-containing (for example methanol), halogenide-containing or sulphur-containing organic compounds to hydrocarbons, in particular, to light olefins, i.e. $C_2$ to $C_4$ olefins, or gasoline and aromatics. In the present application the conversion of said oxygen-containing (also referred to as oxygenates), halogenide-containing or sulphur-containing organic compounds to hydrocarbons, especially light olefins, is referred to as the XTO process. The interest in the XTO process is based on the fact that feedstocks, especially methanol can be obtained from coal, biomass, hydrocarbon residues, petcoke, organic waste or natural gas by the production of synthesis gas, which is then further processed to produce methanol. The XTO process can be combined with an OCP (olefin cracking process) process to increase production of olefins. The XTO process produces light olefins such as ethylene and propylene, as well as heavy hydrocarbons such as butenes and above. These heavy hydrocarbons are cracked in an OCP process to give mainly ethylene and propylene.

In accordance with U.S. Pat. No. 5,573,990 methanol and/or dimethylether is converted to light olefins in the presence of a catalyst, which contains at least 0.7% by weight of phosphorus and at least 0.97% by weight of rare earth elements, which are incorporated within the structure of the catalyst and allegedly enhance the hydrothermal stability of the zeolite. The rare earth elements are preferably rich in lanthanum, the content of lanthanum in the catalyst being preferably comprised between 2.5 and 3.5% by weight of the catalyst. The rare earth elements are introduced via impregnation of the crystal structure with an aqueous solution of a lanthanum salt, for example $La(NO_3)_3$, or of mixed rare earth salts rich in lanthanum. The zeolite ZSM-5 based catalyst presents a mole ratio $SiO_2/Al_2O_3$ comprised between 40 and 80, a crystal size comprised between 1 and 10 μm and adsorption capacities of n-hexane and water of from 10 to 11% by weight and of from 6 to 7% by weight respectively. Said ZSM-5 is synthesized in the presence of a template, then extruded with colloidal silica and converted to the hydrogen form by ion exchange using hydrochloric acid.

US 20060144759 A1 is related to the production of ethylene and propylene from the catalytic cracking of hydrocarbons, which may include an unsaturated bond, but no mention is made of oxygen-containing feedstocks. The aim was to find a catalyst, which could be used in a reactor permitting continuous regeneration of the catalyst. The zeolite thus cited as suitable is a high silica zeolite, preferably a ZSM-5 and/or a ZSM-11, having a $SiO_2/Al_2O_3$ molar ratio ranging from 25 to 800 and carrying a rare earth element preferably chosen from lanthanum, cerium, praseodymium, neodymium, samarium, gadolinium and dysprosium. It is stated that mere physical mixing of the zeolite with the rare earth compound is not sufficient. The zeolite may also contain other components such as an alkali metal, an alkaline earth metal, a transition metal, a noble metal, a halogen and phosphorus.

In accordance with US 2007/0032379 A1, an alkaline earth metal-containing MFI zeolite is disclosed, having a Si/Al atomic ratio of from 30 to 400, an alkaline earth metal/Al atomic ratio ranging from 0.75 to 15, and an average particle diameter ranging from 0.05 to 2 μm. This zeolite is selective for the production of lower hydrocarbons, e.g. ethylene and propylene, from dimethyl ether and/or methanol and is stated to have an extended catalyst life. The zeolite is obtained by synthesising a zeolite raw material solution, which contains a $SiO_2$ source, a metal oxide source, an alkali source and a structure directing agent, i.e. a template, in the presence of an alkaline earth metal salt, such as calcium acetate, and a zeolite seed crystal. This implies that the metal salt is present within the zeolite crystal structure.

According to U.S. Pat. No. 4,049,573, a catalytic process is provided for converting lower monohydric alcohols to a hydrocarbon mixture rich in ethylene and propylene and mononuclear aromatics with a high selectivity for paraxylene, using a catalyst comprising a crystalline aluminosilicate zeolite having a silica to alumina ratio of at least about 12, a constraint index in the range of 1 to 12, said catalyst having been modified by the addition thereto of a minor proportion of an oxide of boron or magnesium either alone or in combination, optionally with an oxide of phosphorus. The zeolite can be ion-exchanged to form metal-modified zeolites for example with nickel, zinc, calcium or rare earth metals.

In accordance with U.S. Pat. No. 3,911,041, methanol or dimethyl ether is subjected to conversion, at a temperature of at least about 300° C., with a catalyst comprising a crystalline aluminosilicate zeolite having a silica to alumina ratio of at least about 12, a constraint index of about 1 to 12, and containing phosphorus incorporated within the crystal structure thereof in an amount of at least about 0.78 percent by weight, preferably not higher than about 4.5 percent by weight. The zeolite, preferably, also has a dried crystal density of not less than about 1.6 grams per cubic centimetre. The crystalline aluminosilicate zeolite is first converted to the hydrogen form, then phosphorus is introduced by reaction with a phosphorus-containing compound having a covalent or ionic constituent capable of reacting or exchanging with a hydrogen ion. Thereafter, the phosphorus-modified zeolite is heated. There is no steaming of the zeolite prior to introduction of phosphorus. Preferably, prior to reacting the zeolite with the phosphorus-containing compound, the zeolite is dried, preferably in the presence of air and at an elevated temperature. The phosphorus-containing zeolite thus obtained may be further modified by impregnating the zeolite with zinc. This can be carried out by contacting the zeolite with a solution of a zinc salt, so that the zinc salt can fill the pore volume of the phosphorus-containing zeolite. Zinc-impregnated phosphorus-containing zeolites are claimed to have higher levels of conversion than those zeolites not impregnated with zinc.

Sano et al. (*Applied Catalysis*, 33, 1987, 209-217) discusses the differences of Ca—H-ZSM-5, CaCO$_3$/Ca—H-ZSM-5 and CaO/Ca—H-ZSM-5. The Ca—H-ZSM-5 zeolite was obtained by mixing aluminium nitrate, colloidal silica and calcium acetate, template and sodium hydroxide in solution. Thus, the calcium is contained within the crystal structure of the zeolite. After crystallisation of the zeolite from the hydrogel, the crystals were filtered off and then washed, dried, calcined at 500° C. for 16 hours, protonated and calcined again at 500° C. for 6 hours to obtain CaCO$_3$/Ca—H-ZSM-5. To obtain CaO/Ca—H-ZSM-5, the CaCO$_3$-containing catalyst was calcined once more for a further 24 hours at 600° C. The catalyst stabilities and long-term aging of Ca—H-ZSM-5, CaCO$_3$/Ca—H-ZSM-5 and CaO/Ca—H-ZSM-5 were then compared in methanol conversions. Very slow decays of conversion and selectivity were observed for the CaCO$_3$/Ca—H-ZSM-5 and the CaO/Ca—H-ZSM-5 zeolites. However Ca—H-ZSM-5 decayed rapidly, which is claimed to be due to the increased coke deposition on the catalyst surface. The amount of coke deposited on the CaCO$_3$/Ca—H-ZSM-5 and the CaO/Ca—H-ZSM-5 zeolites was far less. On the other hand, the modification of the calcium-containing catalyst to a CaCO$_3$- or CaO-containing catalyst did not seem to affect resistance to steaming. Thus, the extended catalyst life was attributed to the improved resistance to coking and not to the improved resistance to hydrothermal treatment. All of the H-ZSM-5 disclosed by Sano et al. are phosphorous free.

WO2007/043741 discloses a catalyst for producing light olefins from a hydrocarbon feedstock wherein the catalyst consists of a product obtained by the evaporation of water from a raw material mixture comprising 100 parts by weight of a molecular sieve with a framework of Si—OH—Al groups, 0.01-5.0 parts by weight of a water-insoluble metal salt, and 0.05-17.0 parts by weight of a phosphate compound. Thus the phosphorus and the metal salt compound are added simultaneously. It is stated that the metal salt compound thereby stabilises the phosphate ion species without ion exchange with the protons of the molecular sieve. The water-insoluble metal salt is a metal salt with a solubility product (Ksp) of less than $10^{-4}$, i.e. a pKsp of more than 4. This includes oxides, hydroxides, carbonates or oxalates of metals with an oxidation state of more than +2, preferably alkaline earth metals (Mg, Ca, Sr, and Ba), transition metals (Ti, V, Cr, Mn, Fe, Co, Ni, and Cu) and heavy metals (B, Al, Ga, In, Ti, Sn, Pb, Sb and Bi). There is also no indication that this catalyst can be used in XTO processes.

WO2006/028333 discloses a porous solid acid catalyst for producing light olefins from hydrocarbon feedstocks. The catalyst is prepared by carrying out a pillaring reaction of a raw material mixture comprising 42-60 wt % HZSM-5 having a Si/Al molar ratio of 15-300, 12-38 wt % layered compound, 1-20 wt % Al$_2$O$_3$ as a pillaring agent, 1-4 wt % P$_2$O$_5$, 10-15 wt % SiO$_2$ and 0.5-2.5 wt % B$_2$O$_3$ based on an oxide form in water.

Fujisawa et al. (*Bull. Chem. Soc. Jpn.*, 60, 1987, 791-793) discusses the production of light olefins from methanol using phosphorous free H-ZSM-5 zeolites containing alkaline earth metals. The alkaline earth metals were added to the zeolites in the form of their water-soluble acetates.

According to U.S. Pat. No. 4,544,793, a synthetic zeolite for converting methanol and/or dimethyl ether into lower olefins was obtained with a phosphorous free crystalline aluminosilicate having the empirical formula xM$_2$O.yM'O.Al$_2$O$_3$.zSiO$_2$.nH$_2$O wherein M is an exchangeable cation selected from the group consisting of alkali metals, hydrogen and mixtures thereof, M' is an alkaline earth metal and x is between 0 and 1.5, y is between 0.2 and 40, z is between 12 and 3000 and n is between 0 and 40, wherein x+y is 1.2 or more, and the aluminosilicate has a specific X-ray diffraction pattern.

Metal modified zeolites, particularly, P-zeolites and their use as XTO catalysts are known in the art. Typically, non-dealuminated zeolites obtained by direct synthesis were modified with P by impregnation techniques and then promoted with rare earth elements or Mg. This modification aims to additionally stabilize the phosphorous on the zeolite by means of formation of complex metal-aluminophosphates. These species are more resistant in a hydrothermal environment and protect the aluminium located within the framework against migration.

On the other hand, Ca (calcium) is more typically used as a promoter for phosphorous-free high silica zeolites. This metal is usually not used for P-modified molecular sieves due to very high affinities that Ca exhibits towards P. Typically, calcium interacts mostly with the acid sites in the proximity of the external surface of the zeolite, because of the high diffusion constraint. Higher affinity of Ca towards P in respect of aluminium leads to removal of the phosphorous bound initially to aluminium. This effect leads to recovery of phosphorus free aluminium acid sites, which are far less hydrothermally stable and could promote unwanted side reactions. Therefore, calcium cannot be applied in the case of P-modified molecular sieves in the same manner as, for example, Mg and La, or as calcium was previously used in P-free zeolites. This Ca-comprising compound having Ca present in equal or excess amounts with respect to phosphorous would normally provoke the movement of far too much phosphorous from the microporous structure to the external surface. Therefore, it is important that Ca atoms are saturated with phosphorous.

Thus, use of calcium as a promoter for P-modified molecular sieves requires a special approach. In addition, this approach could be expanded to other alkali-earth metals and also rare-earth metals. This invention proposes a different solution for the preparation of alkaline earth or rare earth metal-P-modified molecular sieves (M-P-modified molecular sieves) consisting in introducing the metal in the form of an alkaline earth or rare earth metal-containing solution (M-containing solution) in the presence of an excess amount of phosphorous in the mixture. The final molar M/P ratio in M-P-zeolite should be lower than 1 and preferably the concentration of the M-containing solution should be at least 0.05-M. The catalyst prepared this way shows a very good performance in XTO and/or OCP processes and provides a superior hydrothermal stability in comparison with M-free P-zeolite. Especially preferred are phosphorus-modified (P-modified) molecular sieves prepared based on zeolites with a low Si/Al ratio, subjected to dealumination by steaming and leaching/P-modification followed by alkaline earth or rare earth metal modifications. Prior dealumination and chemical interaction of aluminum with phosphorus and alkaline earth or rare earth metal inhibit the further dealumination of zeolites, which, in turn, increases their stability and selectivity in XTO.

Thus, the current invention proposes an improved catalyst for XTO and/or OCP processes.

It is thus an aim of the invention is to find a catalyst for XTO and/or OCP processes with an increased yield of light olefins.

It is another aim of the invention to find a catalyst for XTO and/or OCP processes with a higher hydrothermal stability.

In addition, it is another aim of the invention to find a catalyst for XTO and/or OCP processes with reduced selectivity for paraffins.

The invention fulfils at least one of the above aims.

SUMMARY OF THE INVENTION

The present invention covers a process for obtaining an alkaline earth or rare earth metal —P-modified molecular sieve (M-P-modified molecular sieve) comprising the following steps:
- a). selecting at least one molecular sieve selected from one of:
  - a P-modified molecular sieve which contains at least 0.3 wt % of P
  - a molecular sieve which is modified with P prior to or during step b) introducing at least 0.3 wt % of P
- b). contacting said molecular sieve with an alkaline earth or rare earth metal-containing compound (M-containing compound) to introduce at least 0.05 wt % of the alkaline earth or rare earth metal M.

Optionally, the contact of the molecular sieve with the P-containing compound and the -M-containing compound can be performed simultaneously.

The introduction of the alkaline earth or rare earth metal (M) is performed by bringing the molecular sieve in contact with a solution of one or more M-containing compounds. Said solution can contain a higher concentration of the alkaline earth or rare earth metal than that found in the final M-P-modified molecular sieve.

The modification of molecular sieves with phosphorous is known per se. This modification is carried out by treating molecular sieves with P-compounds in aqueous or non-aqueous media, by chemical vapor deposition of organic P-compounds or impregnation. The catalyst can be pre-formulated with binder or not. The preferred P-compounds used typically for this purpose can be selected from the group of phosphoric acid, $NH_4H_2PO_4$ or $(NH_4)_2HPO_4$.

The M-containing compound can be selected from organic compounds, salts, hydroxides and oxides. These compounds may also contain phosphorus. It is essential that these compounds are present in solubilized form, before bringing them into contact with the molecular sieve or by forming a solution when in contact with the molecular sieve.

The final molar ratio M/P in the M-P-molecular sieve is preferably less than 1.

The molecular sieve can be selected from the list of MFI, MOR, MEL, clinoptilolite, FER, FAU, MWW, BETA, MCM-41, ZSM-21, ZSM-22, ZSM-23, ZSM-42, ZSM-57, LTL or a mixture thereof. More preferably, the molecular sieve is selected from the group of MFI, MOR, MEL, clinoptilolite, FER or a mixture thereof. In the case of MFI, the molecular sieve is preferably a ZSM-5 zeolite. In another embodiment, the molecular sieve is preferably obtained without direct addition of template.

Preferably, the average pore size of the molecular sieve is at least 0.5 nm.

Said molecular sieve before modification with M and P, can be calcined, steamed, ion-exchanged, treated with acid solution or it may undergo other treatments leading to dealumination. Dealumination of the molecular sieve can be performed simultaneously with the phosphorous modification.

Thus the invention also covers an M-P-modified molecular sieve comprising at least 0.3 wt % of P and at least 0.05 wt % of M, wherein preferably the final molar ratio M/P in the molecular sieve is less than 1.

The invention also covers the catalyst composite comprising:
- a). at least 10 wt % of a alkaline earth or rare earth metal-phosphorus-modified molecular sieve (M-P-modified molecular sieve)
- b). optionally metal phosphates
- c). optionally matrix material
- d). optionally binder Said catalyst composites can be modified by ion exchange, calcination or steaming.

The M-P-modified molecular sieve of the catalyst composite can be made according to the process described above.

The present invention also relates to a process (hereunder referred as "XTO process") for making an olefin product from an oxygen-containing, halogenide-containing or sulphur-containing organic feedstock, wherein said oxygen-containing, halogenide-containing or sulphur-containing organic feedstock is contacted with the above catalyst composite (in the XTO reactor) under conditions effective to convert at least a portion of the oxygen-containing, halogenide-containing or sulphur-containing organic feedstock to olefin products (the XTO reactor effluent). It is desirable to have a substantially 100% conversion of the organic compound in the XTO reactor. This conversion rate is adjusted by optimisation of the contact time and the frequency of regeneration of the catalyst.

According to a specific embodiment, the XTO reactor effluent comprising light olefins and a heavy hydrocarbon fraction is sent to a fractionation section to separate said light olefins from said heavy hydrocarbon fraction; said heavy hydrocarbon fraction is recycled in the XTO reactor at conditions effective to convert at least a portion of said heavy hydrocarbon fraction to olefin products.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

According to another embodiment of the invention said olefin products (the effluent of the XTO) are fractionated to form a stream comprising essentially ethylene and at least a part of said stream is recycled in the XTO reactor to increase the propylene production.

According to another embodiment of the invention both ethylene and the $C_4^+$ can be recycled in the XTO reactor.

The present invention also relates to a process (hereunder referred to as the "combined XTO and OCP process") to make light olefins from an oxygen-containing, halogenide-containing or sulphur-containing organic feedstock comprising:
  contacting said oxygen-containing, halogenide-containing or sulphur-containing organic feedstock in the XTO reactor with the above catalyst at conditions effective to convert at least a portion of the feedstock to form an XTO reactor effluent comprising light olefins and a heavy hydrocarbon fraction;
  separating said light olefins from said heavy hydrocarbon fraction;

contacting said heavy hydrocarbon fraction in the OCP reactor at conditions effective to convert at least a portion of said heavy hydrocarbon fraction to light olefins. It is desirable to have a substantially 100% conversion of the organic compound in the XTO reactor. This conversion rate is adjusted by optimization of contact time and the frequency of regeneration of the catalyst.

The catalyst composite of the invention can also be used only in the OCP process i.e. the process for the catalytic cracking of an olefin-rich feedstock which is selective towards light olefins in the effluent, the process comprising contacting a hydrocarbon feedstock containing one or more olefins, with a catalyst composite according to the invention, to produce an effluent with an olefin content of lower molecular weight than that of the feedstock.

The catalyst composites according to the invention show high propylene yields, high propylene/ethylene ratios, high stability, high propylene purity and reduced selectivity to paraffin's and to aromatics in the XTO process. These catalysts also provide the additional flexibility for ethylene and $C_4^+$ recycling to increase propylene production. The average propylene yield can be substantially enhanced by using the catalyst composite of the invention in a combination of XTO and OCP process.

DETAILED DESCRIPTION OF THE INVENTION

The molecular sieves that can be used in the invention are preferably zeolites, for example crystalline silicates, more precisely aluminosilicates. Crystalline silicates are microporous crystalline inorganic polymers based on a framework of $XO_4$ tetrahydra linked to each other by sharing oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high surface area; uniform pores with one or more discrete sizes; ion exchangeability; good thermal stability; and ability to adsorb organic compounds. Since the pores of these crystalline aluminosilicates are similar in size to many organic molecules of practical interest, they control the ingress and egress of reactants and products, resulting in particular selectivity in catalytic reactions.

The selected molecular sieves can be made with the help of the seeding technique, but advantageously they are made without template. However, the seeds themselves may have been made with a template, which means in this case that the molecular sieve is made without direct addition of a template. It is preferred that the molecular sieve used in the invention is made without direct addition of template.

The selected molecular sieve according to the present invention has an average pore size of at least 0.5, preferably from 0.5 to 10, more preferably from 0.5 to 5 and most preferably at least from 0.5 to 0.9 nm. The average pore size is determined according to the procedure of the International Zeolite Association.

The selected molecular sieve has an initial atomic ratio Si/Al of at least 4 and not greater than 500. The Si/Al atomic ratio is measured by chemical analysis, for example using XRF. It includes only those Al that are part of the framework structure of the molecular sieve.

As regards to the selected molecular sieve, advantageously it is selected from the group of MFI, MOR, MEL, clinoptilolite, FER, FAU, MWW, BETA, ZSM-21, ZSM-22, ZSM-23, ZSM-42, ZSM-57, LTL or mixtures thereof, according to the International Zeolite Association (*Atlas of Zeolite Structure Types*, 1987, Butterworths). Preferably it is selected from group of the MFI, MOR, MEL, clinoptilolite, FER or a mixture of thereof. More preferably, the MFI is a ZSM-5 zeolite.

In another embodiment, the molecular sieve selected from the group of MFI, MOR, MEL, clinoptilolite, FER or a mixture of, is preferably obtained without direct addition of template.

Prior to P-modification and/or to the alkaline earth or rare earth metal-modification (M-modification), the molecular sieve may undergo further treatments including steaming, leaching (e.g. acid leaching), washing, drying, calcination, impregnation and ion exchanging steps. In addition or alternatively, these steps can also be carried out during or after P-modification. By ion exchanging steps, it is meant herein that at least a portion of the cations originally comprised in the crystal structure are replaced with a wide variety of other cations according to techniques well known in the art. The replacing cations can be hydrogen, ammonium or other metal cations, including mixtures of such cations.

For the purposes of this invention, modification of the molecular sieve with P must be carried out prior to or during M-modification, if the selected molecular sieve is not already P-modified. Preferably, the P-modification is carried out via a dealuminating steaming step followed by a leaching step using any acidic solution containing a source of P, preferably a solution of phosphoric acid. Preferably, the P-modified molecular sieve comprises at least 0.3% of phosphorus by weight of the molecular sieve.

According to one embodiment of the invention, the molecular sieve can be modified with phosphorus according to the process comprising the following steps, in the order given:

steaming of the molecular sieve at a temperature ranging from 400 to 870° C. for 0.01-200 h;
  leaching with an aqueous acid solution containing the source of P at conditions effective to remove a substantial part of Al from the molecular sieve and to introduce at least 0.3% of phosphorus by weight of the molecular sieve;

Further modification can then be carried out according to the following steps, in the order given:

separation of the solid from the liquid;
  an optional washing step or an optional drying step or an optional drying step followed by a washing step;
  a calcination step.

Preferably, separation, optional washing and drying steps and calcination are carried out after introduction of the M-containing compound to the molecular sieve. The metal M can be any alkaline earth or rare earth metal. Preferably the alkaline earth metal is Ca. However, it is also possible to use Mg, Sr and Ba. Possible rare earth metals include La and Ce.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert 0020gas, preferably nitrogen. The steam treatment is preferably carried out for a period of from 0.05 to 200 hours, more preferably from 0.05 to 50 hours. It is generally known by the persons in the art that steam treatment of molecular sieves results in aluminium that leaves the molecular sieve framework and resides as aluminiumoxides in and outside the pores of the molecular sieve. This transformation is known as dealumination of molecular sieves and this term will be used throughout the text.

The treatment of the steamed molecular sieve with an acid solution results in dissolution of the extra-framework aluminiumoxide. This transformation is known as leaching and this term will be used throughout the text. The leaching with an aqueous acid solution containing the source of phosphorus is advantageously made under reflux conditions, meaning boiling temperature of the solution.

Amount of said acid solution is advantageously between 2 and 10 litres per kg of molecular sieve. A typical leaching period is around 0.5 to 24 hours. Advantageously the aqueous acid solution containing the source of P in the leaching step has a pH of 3, advantageously 2, or lower. Advantageously said aqueous acid solution is a solution of phosphorus acids, a mixture of phosphorus acids and organic or inorganic acids or mixtures of salts of phosphorus acids and organic or inorganic acids. The phosphorus acids or the corresponding salts can be of the phosphate ($[PO_4]^{3-}$, being tribasic), phosphite ($[HPO_3]^{2-}$, being dibasic), or hypophosphite ($[H_2PO_2]^{1-}$, being monobasic), type. Of the phosphate type also di- or polyphosphates ($[P_nO_{3n+1}]^{(n+2)-}$) can be used. The other organic acids may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, sulfuric acid or a salt of such an acid (e.g. the sodium or ammonium salts) or a mixture of two or more of such acids or salts.

It has been found that phosphorus acid is very efficient in complexing the extra-framework aluminiumoxides and hence removing them from the molecular sieve solid material. Unexpectedly, a larger quantity of phosphorus than what could be expected from the typical pore volume of the molecular sieve and assuming that the pores of the molecular sieves are filled with the used phosphorus acid solution, stays in the solid molecular sieve material. Both factors i.e. dealumination and the retention of P, stabilise the lattice aluminium in the zeolitic lattice, thus avoiding further dealumination. This leads to a higher hydrothermal stability, tuning of the molecular sieve's properties and adjustment of acid properties, thereby increasing the molecular sieve's selectivity. The degree of dealumination can be adjusted by the steaming and leaching conditions.

Advantageously, the final P-content of the molecular sieve is at least 0.3 wt % and preferably between 0.3 and 7 w %. Advantageously at least 10% of Al have been extracted and removed from the molecular sieve by the leaching. The residual P-content is adjusted by the P-concentration in the leaching solution, separating conditions during the separation of the solid from the liquid and/or the optional washing procedure during which impregnation and/or adsorption can also take place. A drying step can be envisaged between the separation and/or washing steps.

The molecular sieve is then either separated from the washing solution or is dried without separation from the washing solution. Said separation is advantageously made by filtration. Then the molecular sieve is calcined, by way of example, at 400° C. for 2-10 hours.

M-modification of the molecular sieve is carried out either on an already P-modified molecular sieve or during/after the P-modification process. P-modification can be carried out as described above wherein the sieve is dealuminated by steaming, then leached with a P-containing acid solution. In this case, advantageously, treatment of the molecular sieve with the M-containing solution is performed after the leaching or washing step i.e. after the phosphorous compound has been added and P-modification has taken place and before the separation step. However, the introduction of M to the molecular sieve can also be envisaged:

during the leaching step,
before the washing step but after leaching and drying
on calcined molecular sieves that have been contacted with P
on molecular sieve that has not been leached to introduce P but has been contacted with P during the washing step Introduction of M on the molecular sieves can be performed either by impregnation or by adsorption from an aqueous solution of M-containing compounds.

The introduction of the M-containing compound can be done at temperatures ranging from ambient temperature up to the boiling point of the solution.

The concentration of the M-containing compound in the solution is at least 0.05-M, preferably between 0.05 and 1.0-M. The amount of the alkaline earth or rare earth metal (M) in the M-P-molecular sieves can vary from at least 0.05% by weight, preferably 0.05 to 7% by weight, most preferably from 0.1 to 4% by weight.

Prior to formulation of the catalyst composite the molecular sieve may undergo further treatments including steaming, leaching (e.g. acid leaching), washing, drying, calcination, impregnation and ion exchanging steps. In addition or alternatively, these steps can also be carried out after formulation of the catalyst composite.

The alkaline earth or rare earth metal M is preferably selected from one or more of: Mg, Ca, Sr, Ba, La, Ce. More preferably, M is an alkaline earth metal. Most preferably, M is Ca. Particularly in the case of P-modification via steaming and leaching, M can be a rare earth metal such as La and Ce.

The M-containing compound is preferably in the form of an organic compound, a salt, hydroxide or oxide. The compound is preferably in a solubilized form when bringing it into contact with the molecular sieve. Alternatively, the solution of the M-containing compound can be formed after bringing the molecular sieve in contact with said compound.

Possible M-containing compounds include metal M compounds such as metal M sulphate, formate, nitrate, acetate, halides, oxyhalides, borates, carbonate, hydroxide, oxide and mixtures thereof. These can be for example, calcium sulphate, formate, nitrate, acetate, halides, oxyhalides, borates, carbonate, hydroxide, oxide and mixtures thereof.

The M-containing compound may also include other metals chosen from one or more of Mg, Sr, Ba, Ga, Al, Ce, In, Cs, Sc, Sn, Li, Zn, Co, Mo, Mn, Ni, Fe, Cu, Cr, Ti and V. The M-containing compounds may also additionally comprise phosphorus.

Those M-containing compounds, which are poorly water-soluble, can be dissolved to form a well-solubilized solution by heating and/or by modifying the pH of the solution by addition of phosphoric, acetic or nitric acid or corresponding ammonium salts of said acids. The concentration of the M-containing compound is at least 0.05-M.

The alkaline earth and rare earth metals M, in particular Ca, possess a large hydration sphere radius in the hydrated state. Thus, without wishing to be bound by theory, it is thought that the ion exchange reaction with the acid sites located on the inside of the micropore structures of the molecular sieve occurs very slowly. As a result, the chosen metal M exposes only the acid sites located on the external surface of the molecular sieve, and thus increasing the selectivity of the catalyst.

In the case of P-modified molecular sieves, M-modification leads to the formation of mixed M-Al-phosphates on the external surface. Taking into account that phosphorous is bound with the alkaline earth or rare earth metal M more strongly than with Al, this modification leads to stabilization of phosphorous on the external surface of the molecular sieve where the phosphorous is the most labile. However, it is essential, that all the M atoms located on the external surface are saturated with phosphorous. This can be guaranteed in the presence of an excess of phosphorous and by the presence of M in solution form, which is, for example, used to wash the excess phosphorous away preventing a plugging of the entrance to micropores.

Formulation into a catalyst composite can be carried out once the M-P-modified molecular sieve has been obtained i.e. other components may be optionally blended with the molecular sieve. (However, the M-P-modified molecular sieve can also be used as such as a catalyst.)

According to one embodiment, the prepared M-P-modified molecular sieve is co-formulated into a catalyst composite to comprise at least 10% by weight of the M-P-molecular sieve as described herein and at least 0.05% by weight of M and at least 0.3% by weight of phosphorous, both in relation to the weight of the molecular sieve.

In a particular embodiment, the molecular sieve can be combined with other materials that provide additional hardness or catalytic activity to the finished catalyst product. Materials, which can be blended with the molecular sieve, can be various inert or catalytically active matrix materials and/or various binder materials. Such materials include clays, silica and/or metal oxides such as alumina.

According to another embodiment, non-modified molecular sive was first formulated with a binder and a matrix materials and then modified with phosphorous and metals.

According to particular embodiment, molecular sieves was optionally dealuminated and then modified with phosphorous during formulation step. Introduction of the metal can be performed during the formulation step or on the formulated solid.

According to preferred embodiment, molecular sieves was first optionally dealuminated and modified with phosphorous and then formulated. Introduction of the metal is performed simultaneously with modification with phosphorous step or/and on formulated catalyst.

The catalyst composite may also optionally comprise binder and/or matrix material and/or metal phosphate. Preferably, the amount of molecular sieve, which is contained in the final catalyst composite can range from 10 to 90% by weight of the total catalyst composite, more preferably from 20 to 70% by weight. The concentration of M in the formulated catalyst can be higher than the M concentration in the molecular sieve alone, because the binder or matrix material may also contain some M-compounds.

Naturally occurring clays, which can be used as binder, are for example clays from the kaolin family or montmorillonite family. Such clays can be used in the raw state as mined or they can be subjected to various treatments before use, such as calcination, acid treatment or chemical modification.

In addition to the foregoing, other materials which can be included in the catalyst composite of the invention include various forms of metals, phosphates (for instance metal phosphates, wherein the metal is chosen from one or more of Ca, Ga, Al, Ca, Ce, In, Cs, Sr, Mg, Ba, Sc, Sn, Li, Zn, Co, Mo, Mn, Ni, Fe, Cu, Cr, Ti and V), alumina or alumina sol, titania, zirconia, quartz, silica or silica sol, and mixtures thereof. Examples of possible phosphates include amorphous metal phosphates, and metal phosphates such as calcium phosphates e.g. monocalcium phosphate, dicalcium phosphate, dicalcium phosphate dehydrate, α- or ⊖-tricalcium phosphate, octacalcium phosphate, hydroxyapatite etc.

Examples of possibly binary binder compositions include, silica-alumina, silica magnesia, silica-zirconia, silica-thoria, silica-beryllia, silica-titania, calcium-alumina and calcium silicate. Examples of ternary binder compositions include for instance calcium-silica-alumina or silica-alumina-zirconia.

These components are effective in increasing the density of the catalyst and increasing the strength of the formulated catalyst. The catalyst may be formulated into pellets, spheres, extruded into other shapes, or formed into spray-dried particles. Generally, the size of the catalyst particles can vary from about 20 to 50,000 µm. In general, pellets, spheres and extrudates are employed in fixed bed reactors and exhibit a particle size of from about 0.5 mm to 5 mm. In general, spray-dried particles are used in fluidised bed reactors and exhibit a particle size of from about 20 to 200 µm.

In particular, spheres are employed in moving bed reactors and exhibit a size from about 0.5 to 5 mm. Spheres can be made in rotating granulator or by oil-drop methods.

The crystal size of the molecular sieve contained in the catalyst composite, is preferably less than about 10 µm, more preferably less than about 5 µm and most preferably less than about 4 µm. The amount of molecular sieves, which is contained in the final catalyst composite ranges from 10 to 90% by weight of the total catalyst composite, preferably 20 to 70% by weight.

The formulated catalyst composite may undergo further treatments including further steaming, leaching, washing, drying, calcination, impregnations and ion exchanging steps.

With regards to the XTO process, the catalyst composite of the invention is particularly suited for the catalytic conversion of oxygen-containing, halogenide-containing or sulphur-containing organic compounds to hydrocarbons. Accordingly, the present invention also relates to a method for making an olefin product from an oxygen-containing, halogenide-containing or sulphur-containing organic feedstock wherein said oxygen-containing, halogenide-containing or sulphur-containing organic feedstock is contacted with the above catalyst under conditions effective to convert the oxygen-containing, halogenide-containing or sulphur-containing organic feedstock to olefin products (the effluent of the XTO). Said effluent comprises light olefins and a heavy hydrocarbon fraction.

In this process a feedstock containing an oxygen-containing, halogenide-containing or sulphur-containing organic compound contacts the above described catalyst composite in a reaction zone of a reactor at conditions effective to produce light olefins, particularly ethylene and propylene. Typically, the oxygen-containing, halogenide-containing or sulphur-containing organic feedstock is contacted with the catalyst composite when the oxygen-containing, halogenide-containing or sulphur-containing organic compounds are in the vapour phase. Alternately, the process may be carried out in a liquid or a mixed vapour/liquid phase. In this process, converting oxygen-containing, halogenide-containing or sulphur-containing organic compounds, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 600° C. is preferred.

The pressure also may vary over a wide range. Preferred pressures are in the range of about 5 kPa to about 5 MPa, with the most preferred range being of from about 50 kPa to about 0.5 MPa. The foregoing pressures refer to the partial pressure of the oxygen-containing, halogenide-containing, sulphur-containing organic compounds and/or mixtures thereof.

The process can be carried out in any system using a variety of transport beds, particularly a fixed bed or moving bed system could be used. Advantageously a fluidized bed is used. It is particularly desirable to operate the reaction process at high space velocities. The process can be conducted in a single reaction zone or a number of reaction zones arranged in series or in parallel. Any standard commercial scale reactor system can be used, for example fixed bed, fluidised or moving bed systems. After a certain time on-stream the catalyst needs to be regenerated. This regeneration can be carried out in a separate reactor or in the same reactor. In case of a moving bed or fluidised bed reactor, a part of the catalyst is continuously or intermittently withdrawn from the conversion reactor and sent to a second reactor for regeneration. After the regeneration, the regenerated catalyst is continuously or intermittently sent back to the conversion reactor. In the case of a fixed bed reactor the reactor is taken off-line for regeneration. Generally this requires a second spare reactor that can take over the conversion into light olefins. After regeneration the fixed bed reactor is in stand-by until the spare reactor needs regeneration and the regenerated reactor takes over the conversion. Regeneration is carried out by injecting an oxygen-containing stream over the catalyst composite at a sufficiently high temperature to burn the deposited coke on the catalyst composite. The commercial scale reactor systems can be operated at a weight hourly space velocity (WHSV) of from 0.1 hr$^{-1}$ to 1000 hr$^{-1}$.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), aromatic compounds, and mixtures thereof. The preferred diluents are water and nitrogen. Water can be injected in either liquid or vapour form.

According to a specific embodiment essentially no water (or steam) is injected as a diluent of the feedstock sent to the XTO reactor. However it means that the feedstock can contain the water already contained in the fresh oxygen-containing, halogenide-containing or sulphur-containing organic feedstock or the steam used to engage proper flowing of catalyst in fluidised bed of moving bed reactors of the XTO reactor.

The oxygenate feedstock is any feedstock containing a molecule or any chemical having at least an oxygen atom and capable, in the presence of the above catalyst composite, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts. Analogously to these oxygenates, compounds containing sulphur or halides may be used. Examples of suitable compounds include methyl mercaptan; dimethyl sulfide; ethyl mercaptan; diethyl sulfide; ethyl monochloride; methyl monochloride, methyl dichloride, n-alkyl halides, n-alkyl sulfides having n-alkyl groups of comprising the range of from about 1 to about 10 carbon atoms; and mixtures thereof. Preferred oxygenate compounds are methanol, dimethyl ether, or a mixture thereof.

In the XTO effluent among the olefins having 4 or more carbon atoms, more than 50% by weight are butenes. More than 80% by weight and advantageously more than 85% of the hydrocarbons having 4 carbon atoms or more are C4 to C8 olefins.

According to a specific embodiment the XTO reactor effluent comprising light olefins and a heavy hydrocarbon fraction is sent to a fractionation section to separate said light olefins from said heavy hydrocarbon fraction; said heavy hydrocarbon fraction is recycled in the XTO reactor at conditions effective to convert at least a portion of said heavy hydrocarbon fraction to olefin products.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

According to another embodiment of the invention said olefin products (the effluent of the XTO) are fractionated to form a stream comprising essentially ethylene and at least a part of said stream is recycled in the XTO reactor to increase the propylene production and then the flexibility of ethylene vs propylene production. Advantageously the ratio of ethylene to the oxygen-containing, halogenide-containing or sulphur-containing organic feedstock is 1.8 or less.

According to another embodiment of the invention both ethylene and the $C_4^+$ can be recycled in the XTO reactor.

The present invention also relates to a process (hereunder referred to as a "combined XTO and OCP process") to make light olefins from an oxygen-containing, halogenide-containing or sulphur-containing organic feedstock comprising:

contacting said oxygen-containing, halogenide-containing or sulphur-containing organic feedstock in the XTO reactor with the above catalyst at conditions effective to convert at least a portion of the feedstock to form an XTO reactor effluent comprising light olefins and a heavy hydrocarbon fraction;

separating said light olefins from said heavy hydrocarbon fraction;

contacting said heavy hydrocarbon fraction in the OCP reactor at conditions effective to convert at least a portion of said heavy hydrocarbon fraction to light olefins.

The effluent of the XTO reactor comprising light olefins and a heavy hydrocarbon fraction is sent to a fractionation section to separate said light olefins from said heavy hydrocarbon fraction. With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$. It is desirable to have a substantially 100% conversion of the organic compound in the primary reactor. This conversion rate is adjusted by optimisation of the contact time and the frequency of the regeneration of the catalyst.

With regards to the OCP process, said process is known per se. It has been described in EP 1036133, EP 1035915, EP 1036134, EP 1036135, EP 1036136, EP 1036137, EP 1036139, EP 1194502, EP 1190015, EP 1194500 and EP 1363983 the content of which are incorporated in the present invention. The heavy hydrocarbon fraction produced in the XTO reactor is converted in the OCP reactor, also called an "olefin cracking reactor" herein, to produce additional amounts of ethylene and propylene.

According to a specific embodiment the catalysts found to produce this conversion comprise a P-modified crystalline aluminosilicate of the MFI family or the MEL family. These aluminosilicates have been described above in the description of the molecular sieve.

The P-modified MFI or MEL catalyst having a high Si/Al atomic ratio for use in the OCP reactor of the present invention may be manufactured by removing aluminum from a commercially available crystalline silicate. A typical commercially available silicalite has a silicon/aluminum atomic ratio of around 120. The commercially available MFI crystalline silicate may be modified by a steaming process, which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefinic cracking processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of dealumination of the MFI crystalline silicate. In this way by removing aluminum from the MFI crystalline silicate framework and then removing alumina formed there from the pores, the process aims at achieving a substantially homogeneous dealumination throughout the whole pore surface of the catalyst. This reduces the acidity of the catalyst and thereby reduces the occurrence of hydrogen transfer reactions in the cracking process. The reduction of acidity ideally occurs substantially homogeneously throughout the pores defined in the crystalline silicate framework. This is because in the olefin-cracking process hydrocarbon species can enter deeply into the pores. Accordingly, the reduction of acidity and thus the reduction in hydrogen transfer reactions, which would reduce the stability of the MFI catalyst are pursued throughout the whole pore structure in the framework. The framework silicon/aluminum ratio may be increased by this process to a value of at least about 180, preferably from about 180 to 500, more preferably at least 200, yet more preferably at least 300 and most preferably around 480. Preferably, the leaching step is carried out in the presence of a phosphorus source, enabling the P-modification of the initial molecular sieve. More preferably, the leaching step is carried out with an acid solution such as a solution of phosphoric acid. The P-modified aluminosilicate can thus be used according to the invention. The P-modified MEL or MFI crystalline silicate catalyst may be mixed with a binder, preferably an inorganic binder. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free, although aluminum in certain chemical compounds as in aluminium phosphate's may be used as the latter are quite inert and not acidic in nature. If the binder, which is used in conjunction with the crystalline P-modified silicate, is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst composite for use in an OCP reactor are silica or aluminium phosphates.

The relative proportions of the finely divided crystalline P-modified silicate material and the inorganic oxide matrix of the binder can vary widely. Typically, the binder content ranges from 5 to 95% by weight, more typically from 20 to 50% by weight, based on the weight of the composite catalyst. Such a mixture of crystalline P-modified silicate and an inorganic oxide binder is referred to as a formulated crystalline P-modified silicate. In mixing the catalyst with a binder, the catalyst may be formulated into extended pellets, spheres, extruded into other shapes, or formed into a spray-dried powder.

According to another specific embodiment the catalyst composite for the OCP process comprises a P-modified molecular sieve selected from a group of molecular sieves with a low Si/Al ratio (advantageously lower than 30) being in the $H^+$ or $NH_4^+$-form of MFI, MEL, FER, MOR, clinoptilolite, which have been made preferably without direct addition of organic template. According to another specific embodiment of the invention, the P-modified molecular sieve have been modified with phosphorus according to the same process as described above.

The catalyst composites of the invention can thus be used both in the XTO and in the OCP processes. The catalyst composite in the OCP reactor can be the same as the catalysts of the XTO reactor or they can be different, due to differences in the starting molecular sieve, the P content and so on. The catalyst composite of the invention can also be used only in the OCP process i.e. the process for the catalytic cracking of an olefin-rich feedstock which is selective towards light olefins in the effluent, the process comprising contacting a hydrocarbon feedstock containing one or more olefins, with a catalyst composite according to the invention, to produce an effluent with an olefin content of lower molecular weight than that of the feedstock.

The crystalline P-modified aluminosilicate catalyst composite has structural and chemical properties and is employed under particular reaction conditions during the OCP process whereby the catalytic cracking of the $C_4^+$ olefins readily proceeds. Different reaction pathways can occur on the catalyst. The process conditions are set to have an inlet temperature of around 400° to 600° C., preferably from 520° to 600° C., yet more preferably 540° to 580° C., and an olefin partial pressure of from 0.1 to 2 bars, most preferably around atmospheric pressure. Olefin catalytic cracking may be understood to comprise a process yielding shorter molecules via bond breakage.

In the catalytic cracking process of the OCP reactor, the process conditions are selected in order to provide high selectivity towards propylene or ethylene, as desired, a stable olefin conversion over time, and a stable olefinic product distribution in the effluent. Such objectives are favoured by the use of a low acid density of the catalyst composite (i.e. a high Si/Al framework atomic ratio) in conjunction with a low pressure, a high inlet temperature and a short contact time, all of which process parameters are interrelated and provide an overall cumulative effect.

The process conditions are selected to disfavour hydrogen transfer reactions leading to the formation of paraffins, aromatics and coke precursors. The process operating conditions thus employ a high space velocity, a low pressure and a high reaction temperature. The LHSV ranges from 0.5 to 30 hr$^{-1}$, preferably from 1 to 30 hr$^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The heavy hydrocarbon fraction feedstock is preferably fed at a total inlet pressure sufficient to convey the feedstocks through the reactor. Said feedstock may be fed undiluted or diluted in an inert gas, e.g. nitrogen or steam. Preferably, the total absolute pressure in the second reactor ranges from 0.5 to 10 bars. The use of a low olefin partial pressure, for example atmospheric pressure, tends to lower the incidence of hydrogen transfer reactions in the cracking process, which in turn reduces the potential for coke formation, which tends to reduce catalyst stability. The cracking of the olefins is preferably performed at an inlet temperature of the feedstock of from 400° to 650° C., more preferably from 450° to 600° C., yet more preferably from 540° C. to 590° C., typically around 560° to 585° C.

In order to maximize the amount of ethylene and propylene and to minimize the production of methane, aromatics and coke, it is desired to minimize the presence of diolefins in the feed. Diolefin conversion to monoolefin hydrocarbons may be accomplished with a conventional selective hydrogenation process such as disclosed in U.S. Pat. No. 4,695, 560 hereby incorporated by reference.

The OCP reactor can be a fixed bed reactor, a moving bed reactor or a fluidized bed reactor. A typical fluid bed reactor is one of the fluid catalytic cracking (FCC) type used for fluidized-bed catalytic cracking in the oil refinery. A typical moving bed reactor is of the continuous catalytic reforming type. As described above, the process may be performed continuously using a pair of parallel "swing" reactors. The heavy hydrocarbon fraction cracking process is endothermic; therefore, the reactor should be adapted to supply heat as necessary to maintain a suitable reaction temperature. Online or periodic regeneration of the catalyst may be provided by any suitable means known in the art.

The various preferred catalysts of the OCP reactor have been found to exhibit high stability, in particular being capable of giving a stable propylene yield over several days, e.g. up to ten days. This enables the olefin cracking process to be performed continuously in two parallel "swing" reactors wherein when one reactor is operating, the other reactor is undergoing catalyst regeneration. The catalyst can be regenerated several times.

The OCP reactor effluent comprises methane, light olefins and hydrocarbons having 4 carbon atoms or more. Advantageously said OCP reactor effluent is sent to a fractionator and the light olefins are recovered. Advantageously the hydrocarbons having 4 carbon atoms or more are recycled at the inlet of the OCP reactor, optionally mixed with the heavy hydrocarbon recovered from the effluent of the XTO reactor. Advantageously, before recycling said hydrocarbons having 4 carbon atoms or more at the inlet of the OCP reactor, said hydrocarbons having 4 carbon atoms or more are sent to a second fractionator to purge the heavies. In a preferred embodiment the light olefins recovered from the effluent of the XTO reactor and the light olefins recovered from the fractionator following the OCP reactor are treated in a common recovery section.

Optionally, in order to adjust the propylene to ethylene ratio of the whole process (XTO+OCP), ethylene in whole or in part can be recycled over the OCP reactor and advantageously converted into more propylene. This ethylene can either come from the fractionation section of the XTO reactor or from the fractionation section of the OCP reactor or from both the fractionation section of the XTO reactor and the fractionation section of the OCP reactor or even from the optional common recovery section.

Optionally, in order to adjust the propylene to ethylene ratio of the whole process (XTO+OCP), ethylene in whole or in part can be recycled over the XTO reactor where it combines with the oxygen-containing, halogenide-containing or sulphur-containing organic feedstock to form more propylene. This ethylene can either come from the fractionation section of the XTO reactor or from the fractionation section of the OCP reactor or from both the fractionation section of the XTO reactor and the fractionation section of the OCP reactor or even from the optional common recovery section.

These ways of operation allow to respond with the same equipment and catalyst to market propylene to ethylene demand.

Figure 1:
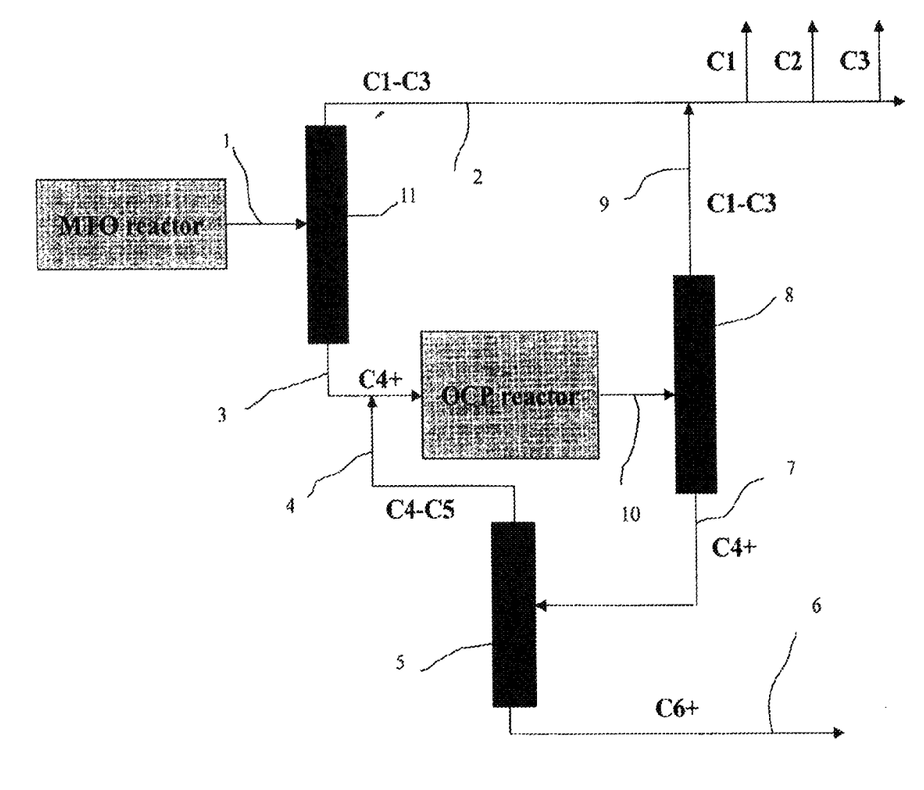
FIGURE illustrates an embodiment including an XTO reactor and an OCP reactor.

FIG. illustrates a specific embodiment of the invention. The effluent of the XTO reactor is passed to a fractionator 11. The overhead, a C1-C3 fraction including the light olefins is sent via line 2 to a common recovery section (not shown). The bottoms (the heavy hydrocarbon fraction) are sent via line 3 to the OCP reactor. The effluent of the OCP reactor is sent via line 10 to a fractionator 8. The overhead, a C1-C3 fraction including the light olefins, is sent via line 9 to a common recovery section (not shown). The bottoms, hydrocarbons having 4 carbon atoms or more, are sent to a fractionator 5. The overhead, hydrocarbons having 4 to substantially 5 carbon atoms are recycled via line 4 at the inlet of the OCP reactor. The bottoms, hydrocarbons having substantially 6 carbon atoms or more, are purged via line 6.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidization in case of gas feedstocks or by reforming or gasification using oxygen and steam in case of solid (coal, organic waste) or liquid feedstocks. Methanol, methylsulfide and methylhalides can be produced by oxidation of methane with the help of dioxygen, sulphur or halides in the corresponding oxygen-containing, halogenide-containing or sulphur-containing organic compound.

One skilled in the art will also appreciate that the olefin products made by the oxygenate-to-olefin conversion reaction using the molecular sieve of the present invention can be polymerized optionally with one or more comonomers to form polyolefins, particularly polyethylenes and polypropylenes. The present invention relates also to said polyethylenes and polypropylenes.

The following non-limiting examples are provided to illustrate the invention.

EXAMPLES

Example 1

A sample of zeolite ZSM-5 with Si/Al=12 (CBV2314) from Zeolyst International was first calcined for 6 hours at 550° C. (60°/min heating rate). It was then steamed at 680° C. for 2 hours in 100% $H_2O$. The steamed solid was treated with a 3.14-M solution of $H_3PO_4$ for 18 h under reflux conditions (4.2 liter/1 kg of zeolite). The solid was then separated by filtration from the solution. The obtained solid was dried first at 110° C. for 16 h and then calcined at 400° C. for 3 h (P-content 5.2 wt %).

Example 2

The sample prepared according to example 1 was subjected to reflux conditions for 2 hours in contact with hot water. Then the solid was separated by filtering from the solution and dried immediately at 110° C. for 16 hours and steamed at 600° C. for 2 hours. (Atomic ratio Si/Al=15, P-content 2.0 wt %). This sample contains no calcium.

The sample is hereinafter identified as Comparative I.

Example 3

This example demonstrates the effect of Ca addition on the catalyst performance.

The sample prepared according to example 1 was impregnated with an aqueous solution of 0.5M calcium acetate (1 ml/1 g of zeolite) corresponding to 2 grams of Ca per 100 grams of zeolite. The sample was then dried at 110° C. and subjected to reflux conditions in contact with hot water (4.2 ml/g zeolite) for 2 h. The solid was separated by filtration from the solution and dried immediately at 110° C. for 16 h and steamed at 600° C. for 2 h. (Atomic ratio Si/Al 15, P content 2.1 wt %, Ca content 0.3 wt %, P/Ca~9).

The sample is hereinafter identified as SAMPLE A.

Example 4

A sample of zeolite ZSM-5 with Si/Al=12 (CBV2314) from Zeolyst International was first calcined for 6 hours at 600° C. (60°/min heating rate). Then it was steamed at 550° C. for 6 hours in 100% $H_2O$. The steamed solid was treated with a 3.14-M solution of $H_3PO_4$ for 18 h under reflux conditions (4.2 liter/1 kg of zeolite). The solid was then separated by filtration from the solution. The obtained solid was dried at 110° C. for 16 h. (P-content 6.3 wt %)

Example 5

The sample prepared according to the example 4 was contacted with an aqueous 0.1-M solution of calcium acetate (4.2 ml/g zeolite) corresponding to 1.68 g of Ca per 100 g of zeolite and stirred for 1 h at room temperature. The solid was separated by filtration from the solution and dried immediately at 110° C. for 16 h and steamed at 600° C. for 2 h in 100% $H_2O$. (Si/Al=17, P-content 2.1 wt %, Ca content 0.2 wt %, P/Ca~13).

The sample is hereinafter identified as SAMPLE B.

Example 6

This example demonstrates the effects of lanthanum salts instead of calcium.

The sample prepared according to the example 4 was contacted with an aqueous 0.1-M solution of lanthanum nitrate (4.2 ml/g zeolite) corresponding to 5.83 g La per 100 g of zeolite during 1 h under stirring at room temperature. The solid was separated by filtration from the solution and dried immediately at 110° C. for 16 h and steamed at 600° C. for 2 h in 100% $H_2O$. (Si/Al=17, P-content 2.4 wt %, La content 3.2 wt %, P/La~3.4).

The sample is hereinafter identified as SAMPLE C.

XTO Process

Catalyst tests were performed on 2 g catalyst samples with a pure methanol feed in a fixed-bed, down flow stainless-steel reactor. Catalyst powders was pressed into wafers and crushed to 35-45 mesh particles. Prior to the catalytic runs all catalysts were heated in flowing $N_2$ (5 Nl/h) up to the reaction temperature. Analysis of the products was performed on-line by a gas chromatograph equipped with a capillary column. The table below presents the average catalytic performance during the cycle (from 2 to 6 h on TOS) at substantially full methanol conversion. The results are displayed on a carbon, water-free basis. The values in Table I are the weight percent on carbon basis. Conditions: WHSV=$4h^{-1}$, P=1.5 bar, T=550° C.

TABLE I

|  | Comparative I | Sample A |
|---|---|---|
| DME + CH3OH as CH2 | 17.7 | 0 |
| Methane | 3.7 | 1.9 |
| Paraffins (non cyclic) | 5.9 | 5.4 |
| Olefins | 65.4 | 84.9 |
| Aromatics | 7.2 | 7.1 |
| Ethylene | 4.4 | 8.5 |
| Propylene | 26.3 | 40.5 |
| Ethylene + Propylene | 30.7 | 49.0 |

Catalyst tests for catalysts SAMPLE B and SAMPLE C were performed under the same conditions. The results are shown in Table II on a carbon, water-free basis.

TABLE II

|  | SAMPLE B | SAMPLE C |
|---|---|---|
| DME + CH3OH as CH2 | 0 | 0 |
| Methane | 1.4 | 1.4 |
| Paraffins (non cyclic) | 6.5 | 9.7 |
| Olefins | 85.6 | 81.9 |

TABLE II-continued

|  | SAMPLE B | SAMPLE C |
|---|---|---|
| Ethylene | 9.1 | 20.0 |
| Propylene | 41.4 | 34.9 |
| Ethylene + Propylene | 50.5 | 54.9 |

The invention claimed is:

1. A process-comprising:
contacting an oxygen-containing organic feedstock in an XTO reactor with a catalyst composite under conditions effective to convert the oxygen-containing organic feedstock to olefin products, wherein an XTO reactor effluent comprising light olefins and a heavy hydrocarbon fraction is sent to a fractionation section to separate said light olefins from said heavy hydrocarbon fraction and wherein the heavy hydrocarbon fraction is sent in an OCP reactor at conditions effective to convert at least a portion of said heavy hydrocarbon fraction to light olefins, wherein a catalyst in the OCP reactor comprises the catalyst composite, wherein the catalyst composite comprises at least 10 weight percent of a modified molecular sieve, wherein the modified molecular sieve comprises:
at least 0.05 weight percent of an alkaline earth metal or a rare earth metal based on a weight of the modified molecular sieve; and
at least 0.3 weight percent of P based on the weight of the modified molecular sieve; and,
wherein the modified molecular sieve is made by a process comprising:
contacting a molecular sieve with a metal-containing compound in aqueous solution form in the presence of excess phosphorus such that the metal atoms located on an external surface of the molecular sieve are saturated with the phosphorus to introduce at least 0.05 wt % of the metal to the molecular sieve;
wherein the metal is an alkaline earth metal or a rare earth metal;
wherein the molecular sieve is selected from a group consisting of MFI, MOR, MEL, clinoptilolite, FER, FAU, MWW, BETA, MCM-41, ZSM-21, ZSM-22, ZSM-23, ZSM-42, ZSM-57, LTL and combinations thereof; and
wherein the molecular sieve that is contacted with the metal-containing compound is a P-modified molecular sieve comprising at least 0.3 wt % of P, and is modified with P by:
steaming the molecular sieve at a temperature ranging from 400 to 870° C. for 0.01-200 hours; and
leaching the molecular sieve with an acid solution comprising a source of P at conditions effective to remove a substantial part of Al from the molecular sieve and to introduce at least 0.3 wt % of P.

2. The process according to claim 1, wherein an XTO reactor effluent comprising light olefins and a heavy hydrocarbon fraction is sent to a fractionation section to separate said light olefins from said heavy hydrocarbon fraction and recycling the heavy hydrocarbon fraction to the XTO reactor at conditions effective to convert at least a portion of said heavy hydrocarbon fraction to olefin products.

3. The process according to claim 1, wherein the olefin products are fractionated to form a stream comprising essentially ethylene, and wherein at least a part of said stream is recycled in the XTO reactor to increase propylene production.

4. The process according to claim 1 wherein OCP reactor effluent is sent to a fractionator and the light olefins are recovered, wherein hydrocarbons having 4 carbon atoms or more of the OCP reactor effluent are recycled at an inlet of the OCP reactor, optionally mixed with heavy hydrocarbon recovered from the XTO reactor effluent.

5. The process according to claim 4, wherein, before recycling said hydrocarbons having 4 carbon atoms or more at the inlet of the OCP reactor, said hydrocarbons having 4 carbon atoms or more are sent to a second fractionator to purge heavies.

6. The process according to claim 1 ethylene in whole or in part is recycled over the OCP reactor wherein said ethylene is from a fractionation section of the XTO reactor a fractionation section of the OCP reactor a fractionation section of the XTO reactor and a fraction section of the OCP reactor, or a common recovery section.

7. The process according to claim 1, wherein ethylene in whole or in part is recycled over the XTO reactor, wherein said ethylene comes from a fractionation section of the XTO reactor, a fractionation section of the OCP reactor, a fractionation section of the XTO reactor and a fraction section of the OCP reactor, or a common recovery section.

8. The process according to claim 1, wherein ethylene is further polymerized optionally with one or more comonomers.

9. The process according to claim 1 wherein propylene is further polymerized optionally with one or more comonomers.

10. The process according to claim 1, wherein the catalyst composite comprises metal phosphate.

11. The process according to claim 1, wherein the catalyst composite comprises matrix material.

12. The process according to claim 1, wherein the catalyst composite comprises binder.

13. The process according to claim 1, wherein a molar ratio of the alkaline earth metal or the rare earth metal to the P (M/P ratio) in the modified molecular sieve is less than 1.

14. The process according to claim 1, wherein an average pores size of the modified molecular sieve is at least 0.5 nm.

15. The process according to claim 1, wherein a crystal size of the modified molecular sieve is less than about 10 μm.

16. The process according to claim 1, wherein the modified molecular sieve was modified with P prior to the introduction of the alkaline earth metal or rare earth metal to the molecular sieve.

17. The process according to claim 1, wherein the alkaline earth metal or rare earth metal comprises one or more of the following metals: Mg, Sr, Ba, Ga, Al, Ce, In, Cs, Sc, Sn, Li, Zn, Co, Mo, Mn, Ni, Fe, Cu, Cr, Ti and V.

18. The process according to claim 1, wherein the modified molecular sieve comprises MFI.

19. The process according to claim 1, wherein the modified molecular sieve comprises ZSM-5.

20. The process according to claim 1, wherein the modified molecular sieve was modified with P by dealuminating the molecular sieve in a steaming step, followed by a leaching step using an acid solution containing a source of P.

21. The process according to claim 1, wherein the modified molecular sieve was modified with P according to the following steps in the order provided:
a) steaming at a temperature ranging from 400 to 870 ° C. for 0.01-200 hours;
b) leaching with an aqueous acid solution containing a source of P at conditions effective to remove a substantial part of Al from the molecular sieve and to introduce at least 0.3 wt % of P.

22. The process according to claim 21, wherein the modified molecular sieve was further modified according to the following steps in the order provided:
  c) separation of solid from liquid;
  d) an optional washing step or an optional drying step or an optional washing step followed by a drying step; and
  e) a calcination step.

23. The process according to claim 1, further comprising:
  contacting a molecular sieve with a metal-containing compound in aqueous solution form in the presence of excess phosphorus such that the metal atoms located on an external surface of the molecular sieve are saturated with the phosphorus to introduce the metal to the molecular sieve to obtain the modified molecular sieve;
  wherein the metal is the alkaline earth metal or the rare earth metal, wherein the molecular sieve comprises MFI.

\* \* \* \* \*